US009107564B2

(12) United States Patent
Burcher et al.

(10) Patent No.: US 9,107,564 B2
(45) Date of Patent: *Aug. 18, 2015

(54) ULTRASONIC SYNTHETIC TRANSMIT FOCUSING WITH MOTION COMPENSATION

(75) Inventors: Michael Burcher, Cambridge (GB); Jean-Luc Robert, White Plains, NY (US)

(73) Assignee: Koninklijke Philips N.V., Eindhoven (NL)

( * ) Notice: Subject to any disclaimer, the term of this patent is extended or adjusted under 35 U.S.C. 154(b) by 1092 days.

This patent is subject to a terminal disclaimer.

(21) Appl. No.: 12/299,633

(22) PCT Filed: Apr. 17, 2007

(86) PCT No.: PCT/US2007/066752
§ 371 (c)(1),
(2), (4) Date: Nov. 5, 2008

(87) PCT Pub. No.: WO2007/133879
PCT Pub. Date: Nov. 22, 2007

(65) Prior Publication Data
US 2009/0099456 A1  Apr. 16, 2009

Related U.S. Application Data

(60) Provisional application No. 60/747,149, filed on May 12, 2006.

(51) Int. Cl.
*A61B 8/00* (2006.01)
*A61B 8/14* (2006.01)
(Continued)

(52) U.S. Cl.
CPC ... *A61B 8/00* (2013.01); *A61B 8/12* (2013.01); *G01S 7/52046* (2013.01); *G01S 7/52095* (2013.01)

(58) Field of Classification Search
CPC ........ A61B 8/00; A61B 8/12; G01S 7/52046; G01S 7/52095
USPC ............. 600/437, 459, 443, 447, 463; 702/39
See application file for complete search history.

(56) References Cited

U.S. PATENT DOCUMENTS 5,793,701 A * 8/1998 Wright et al. ..................... 367/7
5,873,830 A   2/1999 Hossack et al.
(Continued)

FOREIGN PATENT DOCUMENTS

WO   0034802   6/2000
WO   0049427   8/2000

OTHER PUBLICATIONS

"Synthetic Aperture Imaging In Medical Ultrasound With Correction For Motion Artifacts" Nock et al, Ultrasonics Symposium 1990, pp. 1597-1601.

*Primary Examiner* — Katherine Fernandez

(57) ABSTRACT

An ultrasonic diagnostic imaging system produces an image with an extended focal range by transmitting a plurality of beams spaced along an array for multiline reception. The receive multilines of a plurality of transmit beams are spatially aligned and are combined with phase adjustment between the respective receive multilines to prevent undesired phase cancellation. The combined multilines produce the effect of an extended transmit focus so that an image produced using the combined multilines exhibits an extended focal range. To prevent motion artifacts the multiline order is adjustable as a function of image motion.

12 Claims, 8 Drawing Sheets

(51) Int. Cl.
*A61B 8/12* (2006.01)
*G01S 7/52* (2006.01)

(56) References Cited

U.S. PATENT DOCUMENTS

| | | | |
|---|---|---|---|
| 6,126,598 A * | 10/2000 | Entrekin et al. | 600/437 |
| 6,231,511 B1 | 5/2001 | Bae | |
| 6,432,056 B1 * | 8/2002 | Cooley et al. | 600/443 |
| 6,482,157 B2 | 11/2002 | Robinson | |
| 6,508,770 B1 | 1/2003 | Cai | |
| 8,317,704 B2 * | 11/2012 | Robert et al. | 600/443 |
| 8,317,712 B2 * | 11/2012 | Burcher et al. | 600/459 |
| 2002/0143253 A1 * | 10/2002 | Robinson | 600/437 |
| 2007/0276236 A1 * | 11/2007 | Jong | 600/437 |

\* cited by examiner

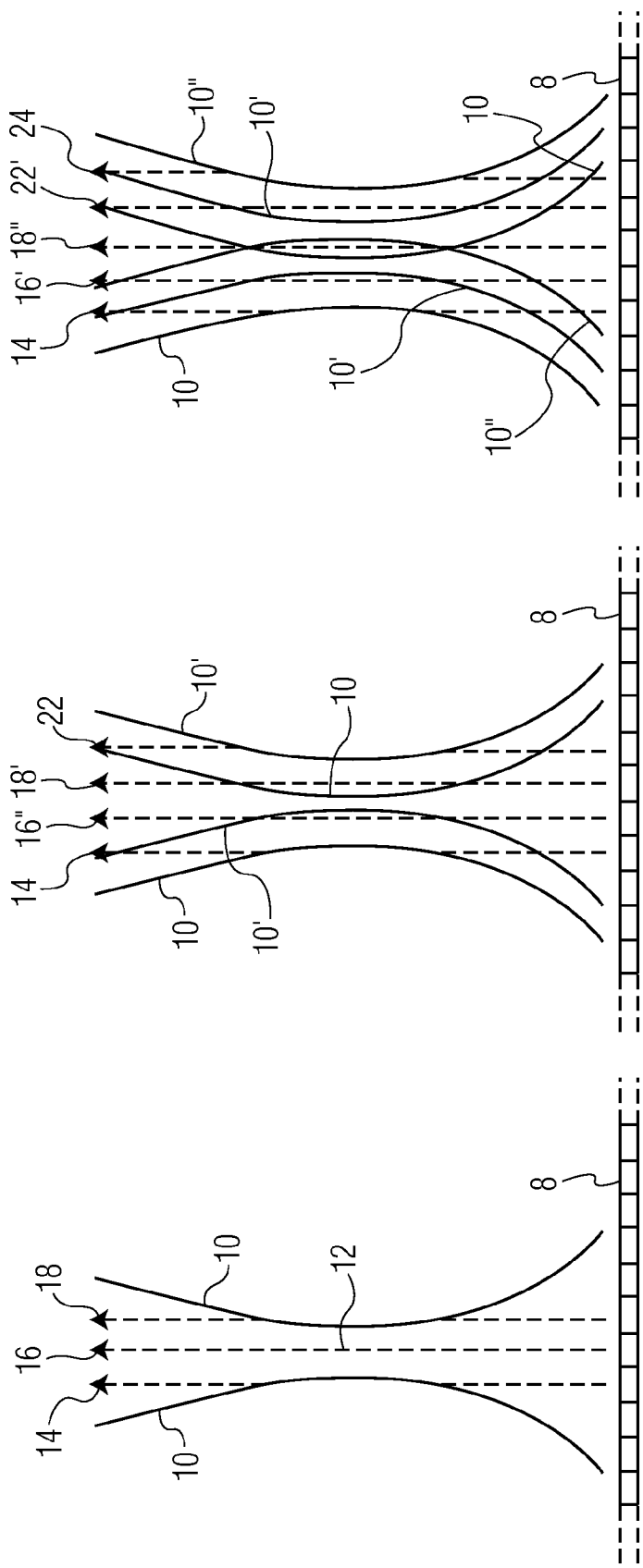

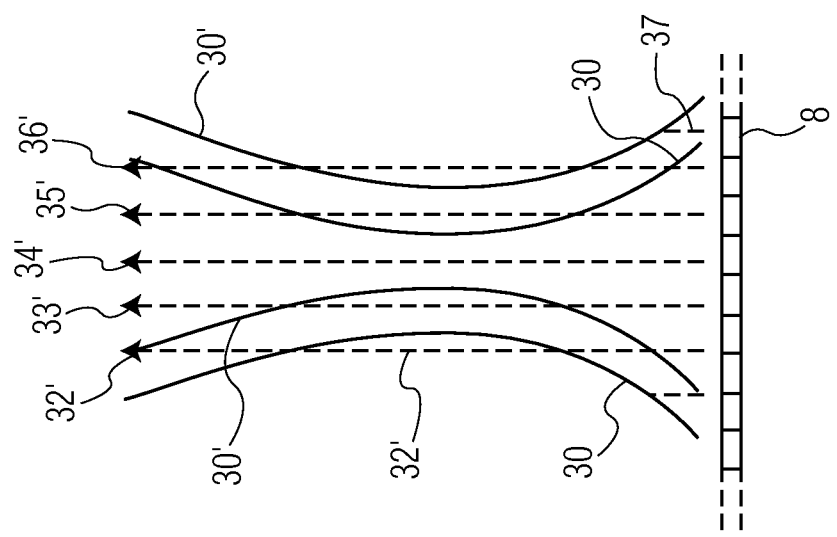
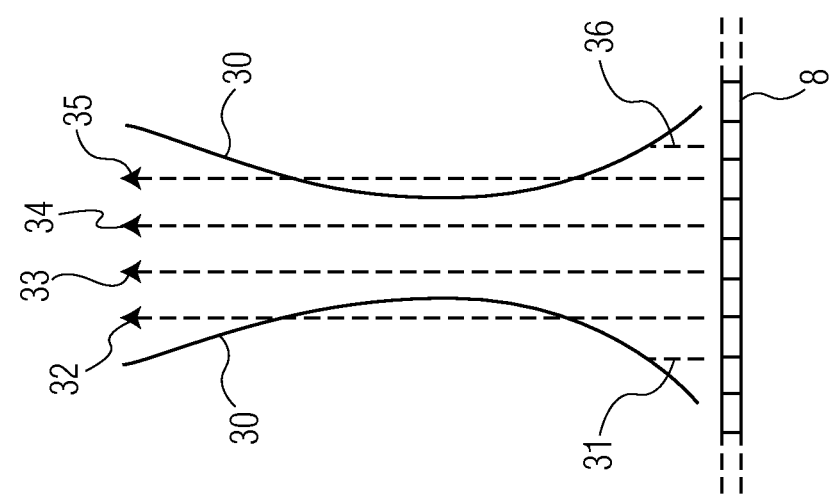

ULTRASONIC SYNTHETIC TRANSMIT FOCUSING WITH MOTION COMPENSATION

This invention relates to medical diagnostic ultrasound systems and, in particular, to ultrasound systems which extend the focal region using a multiline receive beamformer and with reduced motional effects.

The principles of synthetic focusing, by which an ultrasound image is focused at every point in the image field, have been the subject of considerable investigation. For instance, U.S. Pat. No. 4,604,697 (Luthra et al.) describes a synthetic focus technique in which an ultrasound pulse is sequentially transmitted from each element of an ultrasonic transducer array. The echo signals received from each transmission is received by all of the elements of the array and are stored. After all of the signals have been received a focused echo signal can be formed at each point in the image field from the knowledge of the location of each transducer element relative to each point in the image and the time of flight of an ultrasound signal to and from each point. The appropriate received signals are combined to form a coherent echo signal for each point in the image. The selection of the stored data values used to form each point provides the beamformation for each point in the image. While this method will produce a focused signal at every point in the image field, it has several drawbacks. One is that the r.f. signals from the entire image field must be stored for processing. This requires a significant amount of information storage. A second drawback is that a significant amount of processing is required to select and weight the data for each point in the image, then combine the appropriately weighted data to compute the image data points. A third drawback is that this approach is effective for only a shallow penetration depth, since the energy transmitted by a single transducer element is limited.

A specific application which employs the basic principles of synthetic focusing is the traditional delay-and-sum receive beamformer, in which the delays applied to the signals from each receiving element are the equivalent of data selection in the synthetic focus technique. The traditional beamformer is a limited application of these principles as it transmits a transmit beam focused at a specific focal region and dynamically focuses echoes only along this single transmit beam. Multiple transmissions are thus required to scan the entire image field. A resulting efficiency is that data does not need to be stored for all transmissions to every point in the image; the data received from a transmission is immediately processed to form coherent echo signals along the beam direction. A limitation is that each received beam is focused on transmit to only the selected focal region. But the signal-to-noise ratio at greater depths is improved because multiple transducer elements are actuated to transmit a beam, enabling a reasonable penetration to be obtained.

U.S. Pat. No. 6,231,511 (Bae et al.) and a subsequent paper entitled "A Study of Synthetic-Aperture Imaging with Virtual Source Elements in B-Mode Ultrasound Imaging Systems" by Bae et al., IEEE Trans. UFFC, vol. 47, no. 6 (2000) at 1510 et seq. propose to combine aspects of the standard focused beamformer and synthetic focusing to improve lateral resolution outside of the conventional focal region and thus achieve the effect of transmit focusing at all points in the image field. This approach is premised upon the assumption of a "virtual source element" at the focal point of a standard transmitted beam which radiates energy both outward and inward from this "virtual source." Following transmission of a standard transmit focused beam, energy is received by the transducer elements of the receive aperture and stored. After the entire image field has been scanned, an echo signal at each point is computed from the signals received by elements of each virtual source field which encompassed the point in the field. Image points at the focal point will be imaged from only one beam, as the virtual source model is an hourglass-shaped field about the transmit focal point, but points further removed in depth from the focal point are computed from the received signals of many scanlines. The result is said to be an image which shows improved lateral resolution at points outward and inward from the transmit focal point. But like the basic synthetic aperture approach described above, a significant amount of data must be stored for processing, the r.f. signals from every element in each receive aperture. In addition the resultant image is said to appear darker around the focal point, since only one transmission and reception contributes to this image point and its resolution, whereas multiple transmissions and receptions contribute to points removed from the transmit focal point. Accordingly it is desirable to effect transmit focusing over at least a significant portion of an image but without the need to store vast amounts of r.f. data.

In accordance with the principles of the present invention, a diagnostic ultrasound system and method are described which effect transmit focus over a significant depth of field without the need to store r.f. signal data. An ultrasound beam is transmitted which insonifies at least portions of multiple scanline locations and receive beams are concurrently processed along the multiple scanlines, e.g., in parallel or by time multiplexing. A succession of such transmissions produces multiple scanlines related to a common scanline location. The related scanline data is combined to produce echo data which is effectively transmit focused over a significant depth of field. The number of scanlines from multiple transmit intervals which is combined is a function of detected motion. In an example described below, an ultrasound system receives the simultaneous beams with a multiline beamformer. An implementation of the present invention can improve the frame rate of ultrasound imaging in the presence of motion by reducing the need to resort to multizone focusing in some clinical applications.

In the drawings:

FIGS. 1a-1c illustrate beam profiles of a three-beam example of the present invention.

FIGS. 2a-2d illustrate beam profiles of a six-beam example of the present invention.

Figure 2D:
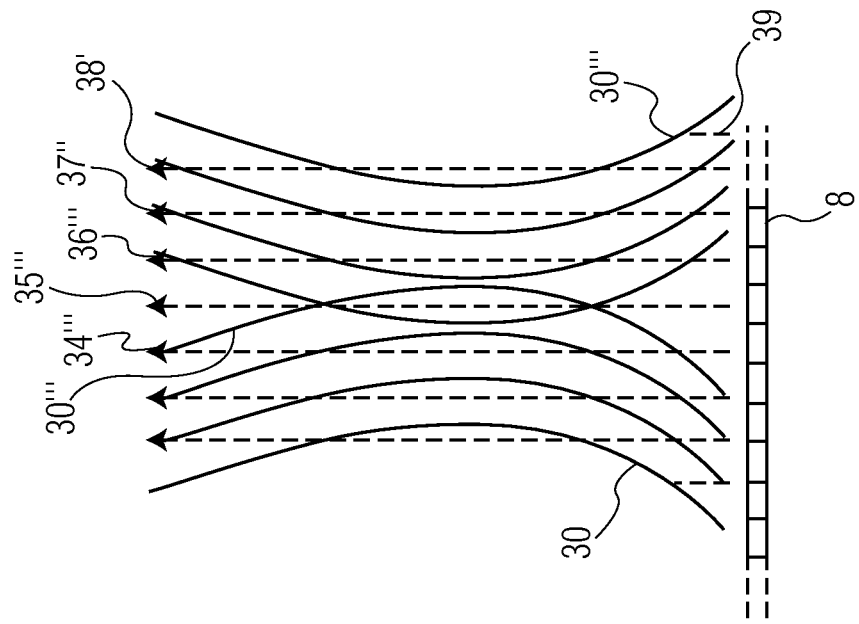

Referring first to FIGS. 1a-1c, overlapping beam profiles are shown for the transmission of three transmit beams followed in each case by the reception of three beams from each transmit beam. FIG. 1a shows the transmit beam profile 10 at a constant level below the intensity peak at the center of the beam, transmitted by and extending from a transducer array 8 that transmitted the beam. The transmit beam profile level is chosen by the designer and may be 3 dB, 6 dB, 20 dB, or some other level below the maximum intensity at the center of the beam. The beam profile is seen to be focused about a focal point 12 at the narrowest width of the beam profile by conventional transmit focusing. An orthogonal view of the beam 20 is shown below the transducer array 8 which is seen to comprise a center lobe 20a and side lobes on either side of the main lobe 20a. The transmitted beam reaches its tightest focus at the focal region 12 and diverges thereafter. In other implementations a diverging transmit beam may be used. Focusing at a considerable depth has also been found to be effective.

The transmit beam 10, 20 is transmitted with a width that encompasses multiple receive lines 14, 16, and 18. Generally a wider beam is produced by transmitting from a smaller transmit aperture. That is, a lesser number of elements of the array 8 are actuated to transmit the beam than the total number of elements across the array. Following transmission echoes are received and focused along three receive line locations 14, 16 and 18. As discussed below, the echoes received by the transducer elements of the receive aperture are delayed and summed in three different ways to form multiple lines at different line locations 14, 16, and 18 in response to one transmit beam. In this example receive line 14 is received down the center of the transmit beam 10, 20 and receive lines 14 and 18 are laterally steered and focused to be received on either side of the center line. In this example only the near field and far field portions of the outer lines 14 and 18 are within the transmit beam profile 10. In these regions the outer lines 14 and 18 are received from transmit energy on either side of the center line position thereby sampling targets in the image field on both sides of the center line position, thereby efficiently using the laterally spread energy of the transmit beam in the near and far fields for image reception and resolution.

In FIG. 1b a second beam has been transmitted by shifting the transmit aperture to the right by the spacing of one receive line. The second transmit beam has the same beam profile as the first transmit beam and is outlined by beam profile curves 10'. As in the case of the first beam, three receive lines are simultaneously received and beamformed in response to the second transmission at receive line locations 16', 18' and 22. As a result, receive line 16' is aligned with receive line 16 from the first transmission, receive line 18' is aligned with receive line 18 from the first transmission and receive line 22 is located to the right of the center line 18' of the second transmission. Like the first set of receive lines, the second set of receive multilines 16', 18', and 22 is saved for subsequent processing.

In FIG. 1c a third beam has been transmitted from a center aperture location which is again shifted to the right by one receive line. This transmit beam is outlined by beam profile 10" and the transmission is followed by the simultaneous reception of three receive lines 18", 22' and 24. These three receive lines, like the previous receive lines, are wholly or partially within the beam profile of their transmit beam with the same spacing as the lines of the preceding beams. As a result, receive line 18" is axially aligned with receive line 18' of the second transmission and receive line 18 of the first transmission, and receive line 22' is axially aligned with receive line 22 of the second transmission. The targets in the path of receive lines 18, 18' and 18" have now been sampled by three receive lines, each by a respectively different transmit beam. These co-aligned beams are combined as described below to produce a line of image data along the line which are focused over a greater depth of field than is the case of any individual line, creating an extended transmit focus effect.

The focusing will be effective over a greater depth of field as the echo energy from three beam transmissions is combined to produce the resultant image data.

Transmission and reception continues across the image field in this manner until the full image field has been scanned. Each time the maximum number of receive lines for a given line location has been acquired, three in this example, the receive lines are processed together to produce a line of image data at that location. There is thus no need to store pre-summed r.f. data from any transmission as the received r.f. signals are beamformed into multiple lines as they are received, and there is only a limited need to store previous lines at a line location until all of the receive lines at the location have been acquired, at which time they can be processed and the line storage freed up for storage of subsequent lines.

FIGS. 2a-2d give another example of the present invention in which the transmit beam profile 30 includes all or portions of receive lines at six receive line locations, identified at 31-36 in FIG. 2a. In this example, unlike the first, there is no receive line at the center of the transmit beam. Instead, central receive lines 33 and 34 are spaced one-half of a receive line spacing on either side of the center of the transmit beam. The outer receive lines 32 and 35 are within the beam profile 30 in the near and far fields, and only near field portions of the outermost receive lines 31 and 36 are within the transmit beam profile. It may be decided not to use these near field line portions 31 and 36 in image data formation as explained below.

Figure 2C:
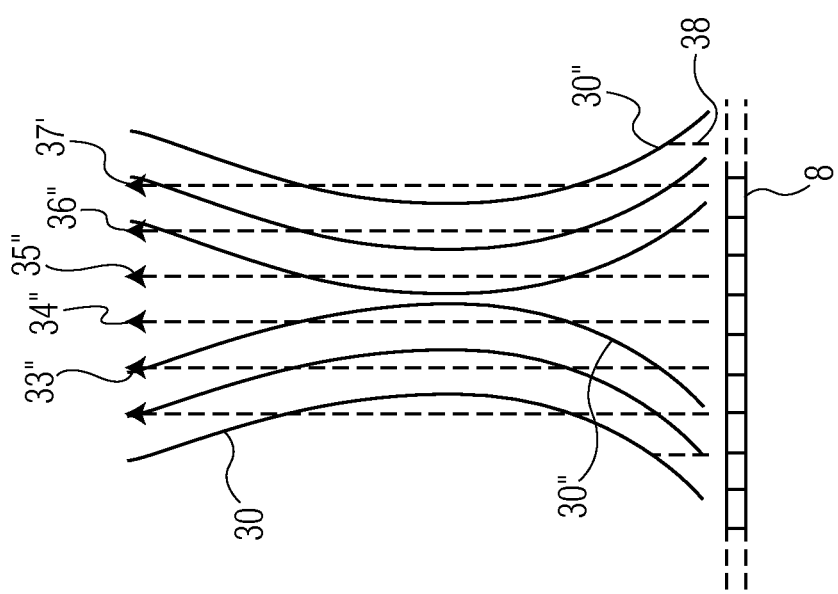
Figure 3A:
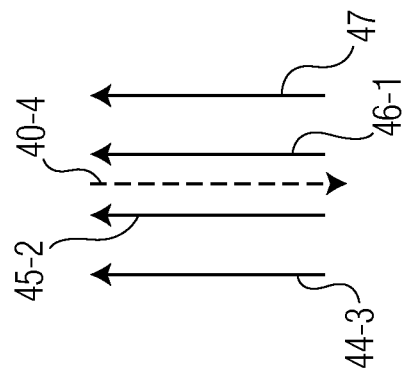
FIGS. 3a-3d illustrate a four-beam example of the present invention in which the first four beam patterns are offset for clarity of illustration.
Figure 3B:
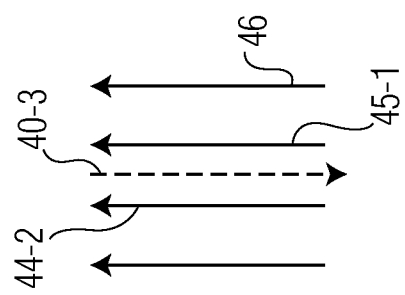
Figure 3C:
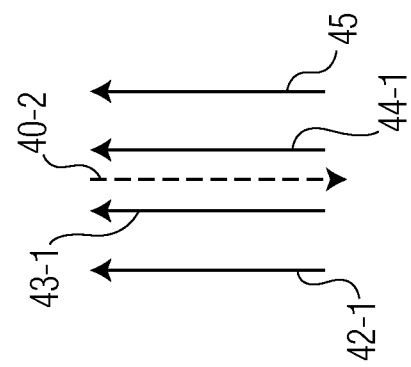
Figure 3D:
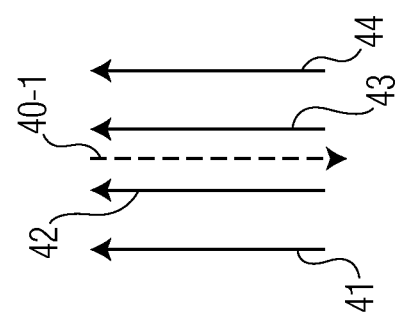
Figure 4A:
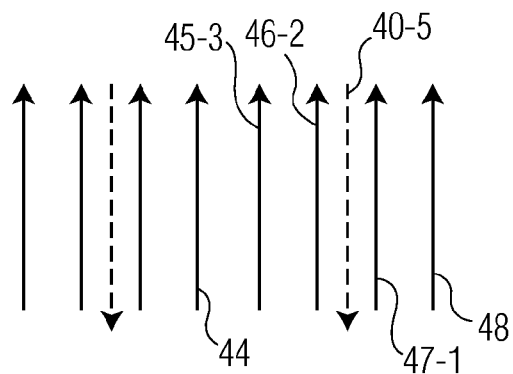
FIGS. 4a-4d illustrate a continuation of the four-beam example of FIG. 3 showing the alignment of the receive beams.
Figure 4B:
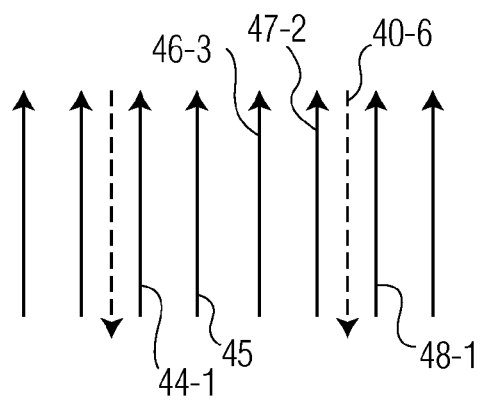
Figure 4C:
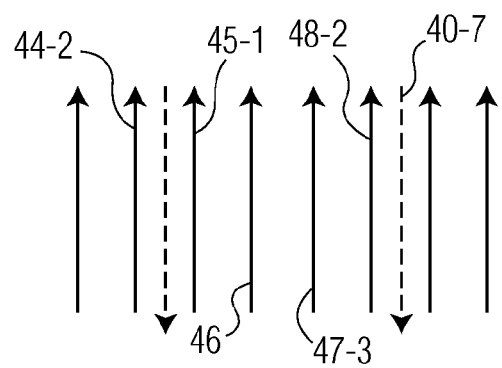
Figure 4D:
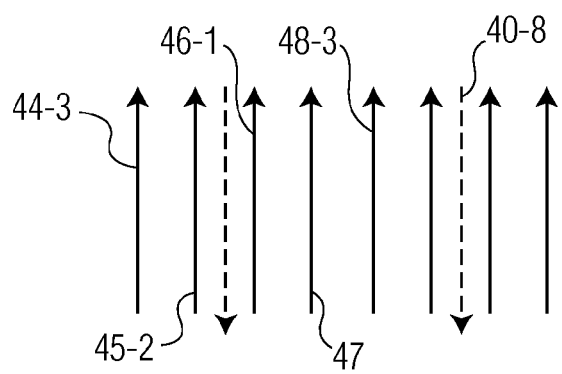

The next transmit beam is transmitted to the right of the first transmit beam by one receive line spacing as shown by the profile 30' of the second transmit beam in FIG. 2b. Six receive lines are again received and beamformed simultaneously at receive line locations 32', 33', 34', 35', 36' and 37. The first five of these receive lines are seen to be aligned with receive lines 32, 33, 34, 35 and 36 of the first transmit beam, thus providing a second receive line for processing at each of these line locations. FIG. 2c shows the results following transmission of a third transmit beam and reception of six receive lines within that beam profile 30". There now have been all or parts of three receive lines received at line locations 33", 34", 35" and 36", two receive lines at location 37', and a portion of one receive line at location 38. Following a fourth transmission, indicated by beam profile 30''' in FIG. 2d, there have been all or portions of four receive lines received at line locations 34''', 35''' and 36''', three receive lines received at line location 37", two receive lines received at line location 38' and a portion of one receive line received at line location 39. It can be seen that, when scanning continues in this manner, there will be all or portions of six receive lines received at the line locations across most of the aperture, except at the extremes where fewer lines will have been received as shown in this example. The greater number of samplings of each receive line location results in better effective transmit focusing when the receive line data is combined to form the image data.

Higher numbers of simultaneously received lines may be used, such as eight, twelve or sixteen spaced apart, simultaneously received lines, for which a lower F number on transmit should be used to insonify the greater expanse of receive line locations.

FIGS. 3 and 4 illustrate another example of the present invention using four receive lines from every transmit beam. In these drawings the successive beam and receive line groups are not overlapping but are vertically aligned for clarity of illustration. Each transmit beam 40-1, 40-2, 40-3, etc. is indicated by a dashed arrow pointing downward, and the receive lines from each transmit beam are shown as solid line arrows on either side of the respective transmit beam. FIGS. 3a-3d illustrate the first four transmit-receive sequences, with the transmit beam 40-n being shifted to the right by one receive line spacing for each successive transmit interval. At the end of this transmit-receive sequence it is seen that four receive lines have been received which are aligned with receive line 44: receive line 44-1 from the second beam, receive line 44-2 from the third beam, and receive line 44-3 from the fourth beam. These four receive lines are combined to produce a line of image data at the location of these receive lines in the image field.

FIGS. 4a-4d show a continuation of the previous transmit-receive sequence with four more transmit-receive intervals of four simultaneously received lines for each transmit beam. The next four transmit beams are identified as 40-5, 40-6, 40-7, and 40-8 in these drawings. As these drawings illustrate, there now have been four receive lines received at line locations 44, 45, 46, 47 and 48. After the four receive lines at each of these locations has been received the four lines can be combined to form one line of image data and the stored receive lines deleted so that subsequent lines can be stored in the same storage locations. Each time another fourth line of a group of four aligned lines has been received, the four lines of the group can be combined to form the line of image data at that location and the storage used for subsequent lines. The sequence continues in this manner, receiving four receive lines for each transmitted beam across the image field so that four receive lines may be combined at each line location over all but the lateral extremities of the image field.

Figure 5:
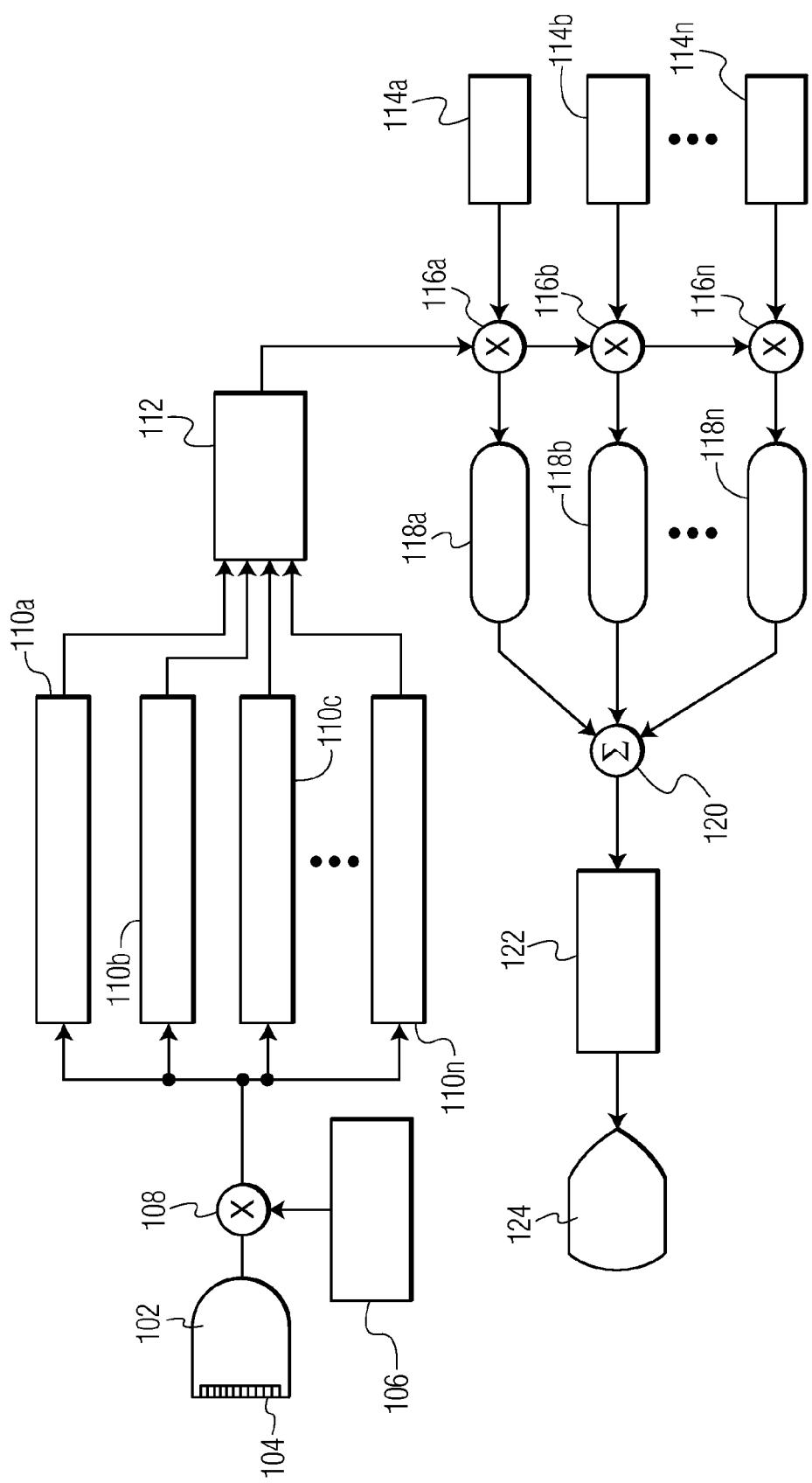
FIG. 5 illustrates in block diagram form an ultrasound system constructed in accordance with the principles of the present invention.

FIG. 5 illustrates in block diagram form an ultrasonic imaging system constructed in accordance with the principles of the present invention. An ultrasonic probe 102 includes a transducer array 104 of transducer elements. Selected groups of the transducer elements are actuated at respectively delayed times by the transmit beamformer 106 to transmit beams focused at selected focal regions in the desired directions and from the desired origin(s) along the array. The transmit beamformer is coupled to the transducer elements by a transmit/receive switch which may comprise a crosspoint switch that protects the receiver inputs from the high voltage transmit pulses applied. The echoes received by each transducer element of the array 104 in response to each transmit beam are applied to the inputs of multiline processors 110a-110n. Each multiline processor comprises a receive beamformer which applies its own set of delays and, if desired, apodization weights to weight the received echoes from the array elements to form a differently steered receive beam from the same transmit beam. Suitable multiline beamformers for the multiline processors 110a-110n may be found, for instance, in U.S. Pat. No. 6,695,783 (Henderson et al.) and U.S. Pat. No. 5,318,033 (Savord). The outputs of the multiline processors 110a-110n are coupled to a line store 112 which stores the received multilines at least until all of the multilines needed to form a line of display data have been acquired. The group of multilines used to form a particular line of display data are applied to respective ones of multipliers 116a-116n to produce the display data for the corresponding line location. The echo data from each line may, if desired be weighted by apodization weights 114a-114n. In general, these weights will weight each line as a function of its round-trip impulse response. A suitable weighting algorithm can be derived by letting the term amplitude(x,z) be the insonification amplitude of a point at location (x,z) in the image field by the transmit wave-front, the azimuth position x=0 corresponding to the center axis of the transmit beam. Let X be the azimuth of the received multiline with respect to the transmit beam axis. The weight applied to this received multiline to form a point of the image at depth Z is:

Weight(X,Z)=amplitude(X,Z)

For determination of an appropriate delay characteristic, let propagation_time(x,z) be the propagation time needed by the transmit wavefront to reach a point at location (x,z), the azimuth x=0 corresponding again to the center axis of the transmit beam. Let X be the azimuth of the receive line with respect to the transmit beam axis. The delay applied to this received multiline to form a point of the image at depth Z is:

Delay(X,Z)=propagation_time(X,Z)−propagation_time(0,Z)

where propagation_time(0,Z) is the time to reach a point at the same depth but on-axis.

The functions amplitude(X,Z) and propagation_time(X,Z) may, for example, be obtained from a simulation of the transmit field. An appropriate way to compute the propagation time is to use the phase delay of the field from monochromatic simulation at several frequencies. The amplitude may be computed by averaging the amplitude of the field at several frequencies. In addition, a depth-dependent normalization can be applied to the weights. This multiplies all the weights at a given depth by a common factor. For example, the normalization can be chosen so that speckle regions have uniform brightness with depth. By varying the weights as a function of depth, it is possible to vary the size and shape (apodization) of the aperture dynamically with depth.

The amplitude and propagation time do not need to be derived from a simulation of the exact transmit characteristics used in the system. The designer may choose to use a different aperture size or a different apodization for example.

The echoes from each line are weighted by the multipliers 116a-116n and delayed by delay lines 118a-118n. In general, these delays will be related to the location of the transmit beam center to the receive line location as shown above. The delays are used to equalize the phase shift variance that exists from line to line for the multilines with differing transmit-receive beam location combinations, so that signal cancellation will not be caused by phase differences of the combined signals.

It will be appreciated that in a digital system the delay lines may be effected by storing the weighted multiline echo data in memory and reading the data out at later times which effect the necessary delay. Shift registers of differing lengths and clock signals may also be used to effect a digital delay, or an interpolating beamformer such as that described in the aforementioned U.S. Pat. No. 6,695,783 may be used. The delayed signals are combined by a summer 120 and the resultant signals are coupled to an image processor 122. The image processor may perform scan conversion or other processing to improve the displayed image. The resultant image is displayed on an image display 124.

In the system of FIG. 5 the delay lines 118 and summer 120 effect a refocusing of the signals received from the several receive multilines which are co-aligned in a given direction. The refocusing adjusts for the phase differences resulting from the use of different transmit beam locations for each multiline, preventing undesired phase cancellation in the combined signals. The weights 114 weight the contributions of the multilines in relation to the proximity of the transmit beam to the multiline location, giving higher weight to receive beams with higher signal-to-noise ratios. This results in an extended depth of field along each receive line and an enhanced penetration (improved signal-to-noise ratio) due to the combination of multiple samplings in each receive line direction.

In the example of FIGS. 4a-4d it is seen that each received multiline is only used once in combination with other co-aligned multilines. This means that an implementation of the present invention does not require the second set of weights 114 multipliers 116 and delays 118, because these weighting and delay effects can be implemented with the weights and delays of the multiline processors 110, which can focus the multiline in the proper receive direction and account for phase and transmit beam variation with respect to the multilines with which it is to be combined, all in one process step. After all the multilines for a given line location have been received they are simply summed to provide the display line data. Alternatively each received multiline for a given line location is stored in a line accumulator for that line. Each subsequently received multiline at that line location is added to the contents of the accumulator until the full complement of multilines at that location has been combined in the accumulator. The accumulator contents are then forwarded to the image processor, freeing the accumulator for use for another line location.

Figure 6A:
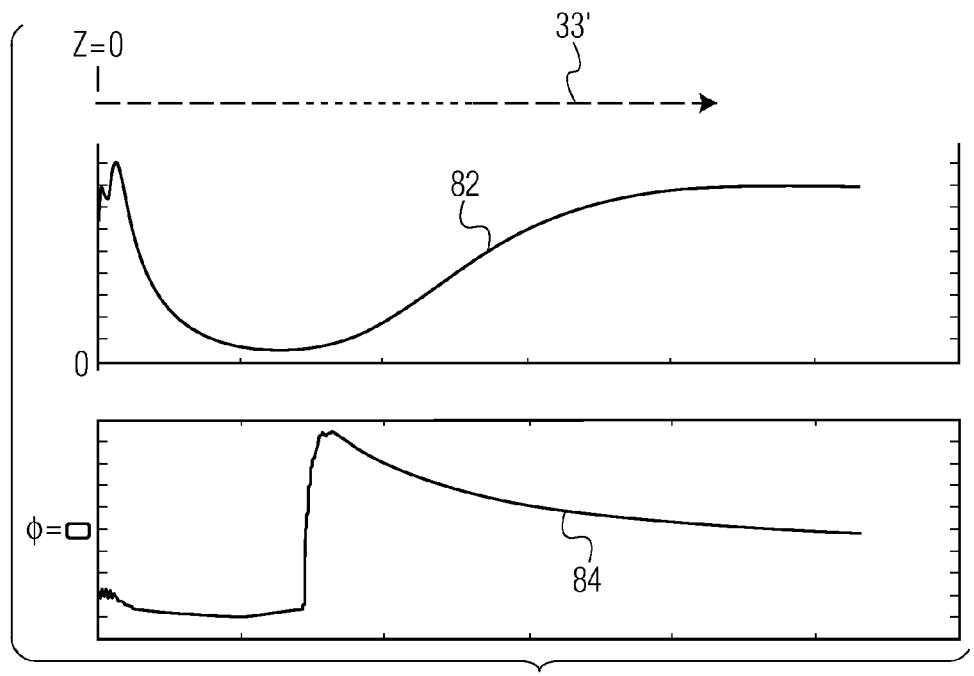
FIGS. 6a and 6b illustrate the delay and weighting characteristics of two different beams of the four-beam example of the present invention.
Figure 6B:
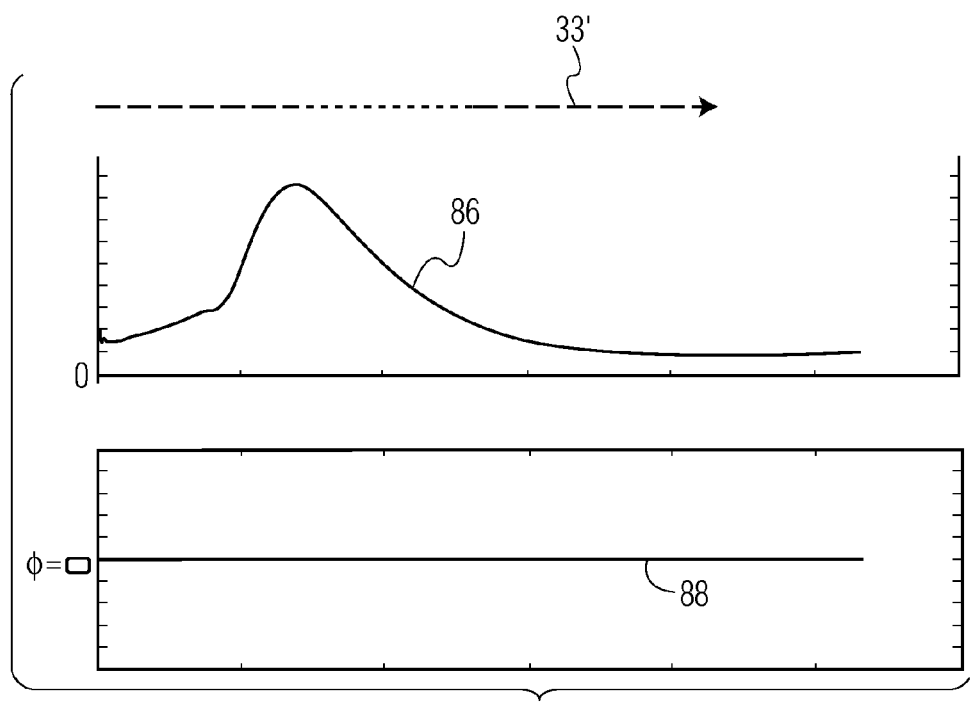

FIGS. 6a and 6b illustrate examples of the weighting and delay characteristics that may be used in combining the received multilines for a given display line location. FIG. 6a illustrates example weighting and delay characteristics for a received multiline that is relatively distant from the transmit beam center such as received multiline 33' of FIG. 2b. The received multiline 33' is shown extending in the z direction from the face of the transducer array at z=0 to the maximum scan depth on the right side of the drawing. The center of the multiline is drawn as dotted where that portion of the multiline 33' is outside of the selected beam profile 30' and its response is below that which the designer has deemed to be acceptable. The weighting characteristic 82 thus weights this multiline with a weight which is at a minimum where it is beyond the beam profile and at nonzero levels where the multiline is to be used for refocusing. In other implementations the weighting characteristic 82 may drop to zero in the near field. This is because the echoes may be too close to or behind the array after the necessary delay has been applied and thus not susceptible to accurate reception. Thus the multilines from laterally distant multilines are not used in the multiline combination in the very near field.

The phase characteristic 84 is seen to cross through a zero phase adjustment at the focal point of the transmit beam, staying nearly constant in the near field and gradually decreasing in the far field.

FIG. 6b illustrates exemplary weighting and delay characteristics for a received multiline 33 that is closer to the center of its transmit beam. Due to this closer proximity the multiline is given greater overall weighting in the combination as shown by the weighting characteristic 86. The weighting increases in the vicinity of the focal region to balance the falloff of the weighting of the more remote multilines such as 33' in this region. The phase adjustment characteristic 88 is drawn as a straight line because the delay characteristic 84 for the more laterally remote multiline is calculated from the phase of the more central multiline 33. In this example the multiline 33 is used for refocusing over the full image depth, although in a given implementation the designer may elect to use the echoes of a single line from a transmit beam in close proximity to the line location in the very near field.

An implementation of the present invention can be used with a variety of receive functions. For instance an implementation can operate on signals from focused sub-apertures. In another variation, instead of forming receive beams per se, a limited number of orthogonal functions such as Fourier components can be used. It is then possible to combine the different transmits in Fourier space. The signals being combined do not correspond exactly to received image lines. Thereafter receive beams are formed by combining the Fourier components or sub-apertures. Various combinations of several beams and functions derived from a beam by a change of apodization are also within the scope of the present invention. In other implementations a small number of received multilines can be increased by interpolating additional intermediate multilines, then performing the inventive processing with the increased number of multilines.

Figure 7:
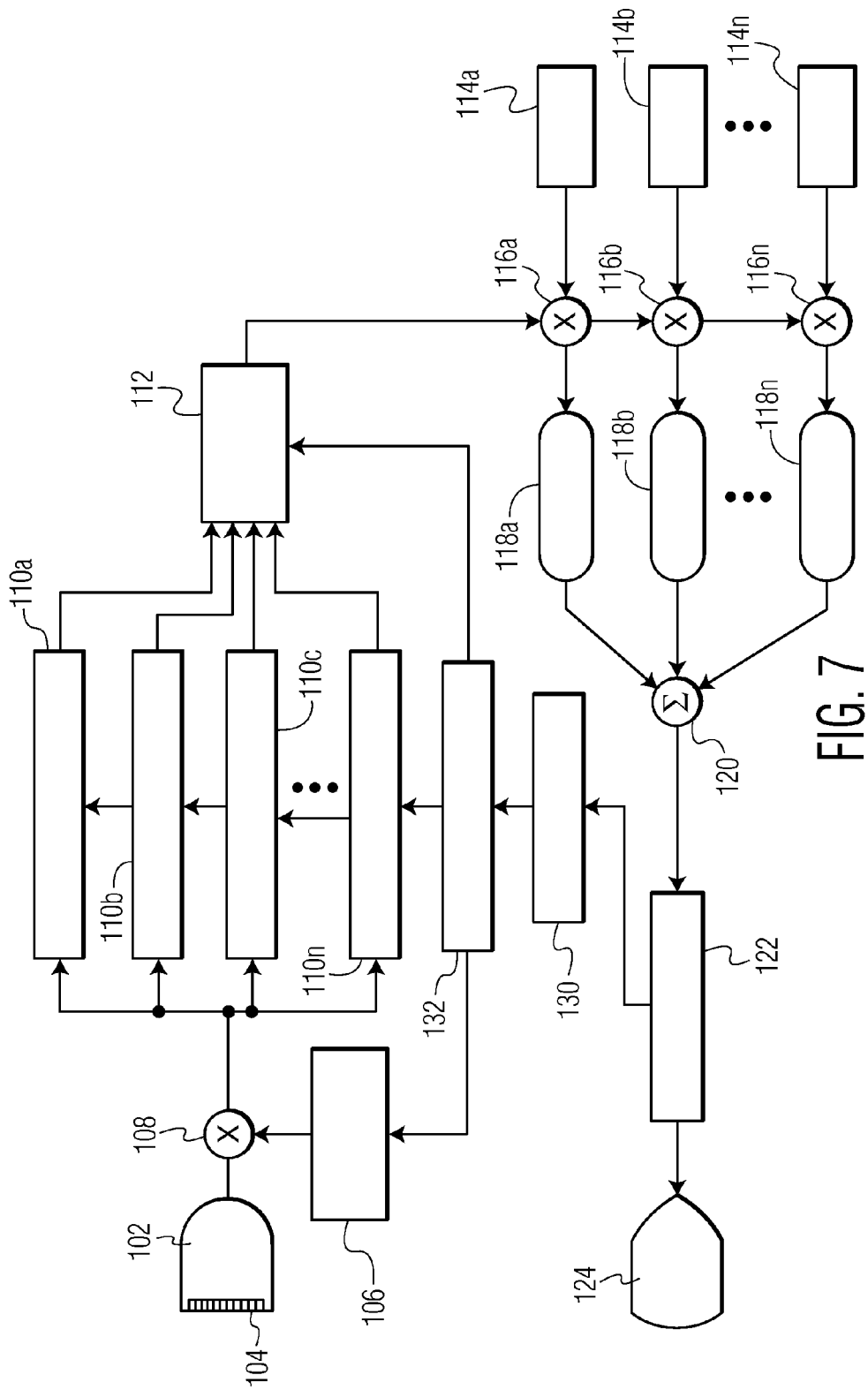
FIG. 7 illustrates in block diagram form an ultrasound system which adaptively responds to motion to adjust the number of multilines being combined in an implementation of the present invention.

FIG. 7 illustrates a variation of the ultrasound system of FIG. 5 in which the effects of motion are addressed. The example shown in FIG. 5 combines the r.f. signals received from a number of co-aligned multilines of different transmit-receive intervals. Since it is r.f. signals and not detected signal envelopes which are being combined, it is important that there be little motion in the image over the period that the multilines which are to be combined are received. Significant motion, either of materials in the image field or of the probe with respect to the image field, can cause r.f. signal differences which result in cancellation rather than the desired signal reinforcement when the signals from the different multilines are combined. This problem is more acute with longer acquisition intervals during which greater numbers of multilines are acquired for combining. The example of FIG. 7 addresses this problem by detecting relative image motion and adjusting the multiline order in response to the presence of motion. A motion detector 130 receives consecutive image frames from the image processor 122 and compares the image content for differences which are indicative of motion. A suitable technique for doing this is a correlation technique which correlates the image pixel values in the same area or areas of consecutive images. This can be done by calculating the zero-lag normalized cross-correlation between the data of the two images. If the correlation factor is high (i.e., the images are nearly identical), a larger number of multilines, requiring a greater number of transmit-receive intervals, are used to improve the depth of field. When the correlation factor is low (the images are different), which can be due to motion within the image field or by the probe, a lesser number of multilines are combined. A suitable correlation technique is the minimum sum of absolute differences (MSAD) technique described in U.S. Pat. No. 6,126,598 (Entrekin et al.) which is incorporated herein by reference. As described in this patent, the data which undergoes MSAD processing for motion detection can be areas of images or reference lines transmitted during or between image frames. Doppler techniques can also be used to detect motion as described in U.S. Pat. No. 5,127,409 (Daigle).

The result of motion detection is coupled to a multiline controller 132 which adjusts the transmission and reception of multilines as a function of motion, with lower order multiline used when motion is present. The adjustments made in this example are in control of the transmit beamformer to transmit a larger F number beam which laterally encompasses fewer multilines when motion is present so that the multilines which are combined span a shorter period of transmit times. Smaller transmit apertures can be used with broader focal regions which are more uniform over a larger range of depths, requiring fewer transmit beams to cover the field of view. On reception the multiline controller 132 controls the number of multiline processors employed, with fewer needed for the reception of fewer multilines in the presence of motion. The multiline controller 132 is also coupled to the line store 112 to command the refocusing of the fewer number of multilines by the weights 114, delay lines 118 and summer 120 when motion is present. The result of these adjustments are that a shorter time is needed to acquire the multilines which are to be combined, the shorter time period being less affected by motion than would a longer acquisition interval. Correspondingly, when the motion detector detects a stationary image field when motional effects are low, the multiline order is increased by the multiline controller. An exemplary adjustment range is to use 16× multiline (receiving sixteen multilines in response to a transmit beam and combining multilines from sixteen transmit beams) when the image field is stationary, and decreasing the multiline order to 8×, 4×, 2× and 1× (single line transmit and receive) as the amount of motion increases. For instance, when the probe is being moved over the body of a subject in a search for certain anatomy or a good viewing perspective, standard single line imaging would be used. The multiline order can also be automatically changed as a function of the imaging mode of the ultrasound system. For instance, when the system is changed from B mode imaging to Doppler imaging, multiline acquisition can be discontinued by the multiline controller. The degree of multiline can be automatically set during imaging by the multiline controller, and/or the user can be provided a manual control to set the degree of multiline.

Variations of the examples above will readily occur to those skilled in the art and are within the scope of the present invention. For example, instead of transmitting along successive line locations, transmission can skip lines (multiplex) between multiline transmission. Transmission can be done along every other line position, every fourth line position, or other intervals of multi-line spacing, thus reducing the number of transmit events needed to form the image and increasing the acquisition rate. This is also a way to reduce motion artifacts. Receiving multilines at more widely spaced line intervals with a fewer number of transmit beams is another way to address the problem of motion. This approach can be augmented with interpolated lines as mentioned above to increase the number of lines which are combined. This will also increase the depth of field improvement for a given number of multilines. The sampling used is generally a function of the F number of the transmit aperture, which determines the Nyquist sampling requirement. Scanning does not have to be done sequentially across the image; other transmission sequences can be used, which will have different responses in the presence of motion. While the examples above are shown with apodization, it is not necessary to apodize on transmission, reception, or multiline combination. It is not necessary that the multilines to be combined all be precisely axially aligned. Multilines which are to be combined can be offset laterally from each other, effecting an interpolation when the multilines are combined. The principles of the present invention are also applicable to three dimensional imaging by performing the processing in both the elevation and azimuth dimensions, and to phased array (sector scan) imaging as well as linear array (orthogonal scan) imaging and by use of curved arrays.

What is claimed is:

1. An ultrasonic diagnostic imaging system for imaging an image field comprising:
   a probe including an array of transducer elements;
   a transmit beamformer, coupled to the array of transducer elements, and operable to transmit a plurality of laterally spaced transmit beams, each encompassing a plurality of laterally spaced line positions;
   a multiline receive beamformer, coupled to the array of transducer elements, which is operable to produce a plurality of receive lines of the image field at the line positions in response to one transmit beam;
   a multiline combining circuit, responsive to a plurality of r.f. receive line signals which relate to a common line position produced by the multiline receive beamformer in response to a plurality of transmit beams, which is operable to delay r.f. receive line signals of a receive line with a phase characteristic which varies as a function of depth and to combine the plurality of r.f. receive line signals to produce transmit refocused image data;
   a motion detector which is operable to detect the presence of motion in the image field; and
   a display which produces an image utilizing the transmit refocused image data,
   wherein a number of the plurality of r.f. receive line signals combined by the multiline combining circuit is a function of the presence of motion.

2. The ultrasonic diagnostic imaging system of claim 1, wherein the multiline combining circuit includes a summer which is operable to combine data from a selected number of different receive lines produced by the multiline receive beamformer.

3. The ultrasonic diagnostic imaging system of claim 2, wherein the multiline combining circuit further includes a plurality of delays responsive to data of different multilines and operable to adjust phase variations between the multilines.

4. The ultrasonic diagnostic imaging system of claim 3, wherein the multiline combining circuit further includes a plurality of weighting circuits which are operable to weight multiline data.

5. The ultrasonic diagnostic imaging system of claim 1, wherein the motion detector further comprises a correlator responsive to image data from different images.

6. The ultrasonic diagnostic imaging system of claim 5, wherein the correlator is operable to produce a correlation factor using a sum of absolute differences calculation.

7. The ultrasonic diagnostic imaging system of claim 1, wherein the transmit beamformer is further operable to transmit a beam exhibiting a beam width which is a function of detected motion in the image field.

8. The ultrasonic diagnostic imaging system of claim 1, wherein the receive beamformer is further operable to produce a number of receive lines which is a function of detected motion in the image field.

9. An ultrasonic diagnostic imaging system for imaging an image field comprising:
   a probe including an array of transducer elements;
   a transmit beamformer, coupled to the array of transducer elements, and operable to transmit a plurality of laterally spaced transmit beams, each encompassing a plurality of laterally spaced line positions;
   a multiline receive beamformer, coupled to the array of transducer elements, which is operable to produce a plurality of receive lines of the image field at the line positions in response to one transmit beam;
   a multiline combining circuit, responsive to a plurality of r.f. receive line signals which relate to a common line position produced by the multiline receive beamformer in response to a plurality of transmit beams, which is operable to delay r.f. receive line signals of a receive line with a phase characteristic which varies as a function of depth and to combine the plurality of r.f. receive line signals to produce transmit refocused image data;
   a motion detector which is operable to detect the presence of motion in the image field; and
   a display which produces an image utilizing the image data, wherein the beams transmitted by the transmit beamformer are a function of the presence of motion.

10. The ultrasonic diagnostic imaging system of claim 9, wherein a lateral dimension of the transmit beams is a function of the presence of motion.

11. The ultrasonic diagnostic imaging system of claim 9, wherein the lateral spacing of the transmit beams is a function of the presence of motion.

12. An ultrasonic diagnostic imaging system for imaging an image field comprising:
- a probe including an array of transducer elements;
- a transmit beamformer, coupled to the array of transducer elements, and operable to transmit a plurality of laterally spaced transmit beams, each encompassing a plurality of laterally spaced line positions;
- a multiline receive beamformer, coupled to the array of transducer elements, which is operable to produce a plurality of receive lines of the image field at the line positions in response to one transmit beam;
- a multiline combining circuit, responsive to a plurality of r.f. receive line signals which relate to a common line position produced by the multiline receive beamformer in response to a plurality of transmit beams, which is operable to delay r.f. receive line signals of a receive line with a phase characteristic which varies as a function of depth and to combine the plurality of r.f. receive line signals to produce transmit refocused image data;
- a motion detector which is operable to detect the presence of motion in the image field; and
- a display which produces an image utilizing the image data,
- wherein a spacing of the line positions used by the multiline receive beamformer is a function of the presence of motion.

* * * * *